United States Patent [19]

Bhattacharjee

[11] Patent Number: 4,812,053
[45] Date of Patent: Mar. 14, 1989

[54] ACTIVATABLE TIME-TEMPERATURE INDICATOR

[75] Inventor: Himangshu R. Bhattacharjee, Randoph, N.J.

[73] Assignee: LifeLines Technology, Inc., Morris Plains, N.J.

[21] Appl. No.: 83,752

[22] Filed: Aug. 7, 1987

Related U.S. Application Data

[63] Continuation of Ser. No. 815,696, Jan. 2, 1986, abandoned.

[51] Int. Cl.$^4$ ............................................. G01K 3/04
[52] U.S. Cl. ...................................... 374/102; 374/162; 116/206; 426/88; 428/913; 252/962; 252/586
[58] Field of Search ...................... 116/206, 207, 216; 252/408.1, 586, 962, 963; 374/102, 106, 161, 162; 422/56–58, 86; 426/88; 428/913; 436/2, 902, 904, 905

[56] References Cited

U.S. PATENT DOCUMENTS

| | | | |
|---|---|---|---|
| 3,018,611 | 1/1962 | Biritz | 116/206 |
| 3,463,532 | 8/1969 | Chidley et al. | 116/206 |
| 3,480,402 | 11/1969 | Jackson | 116/206 |
| 3,768,976 | 10/1973 | Hu et al. | 116/207 |
| 3,966,414 | 6/1976 | Khattab et al. | 116/207 |
| 4,189,399 | 2/1980 | Patel | 252/408.1 |
| 4,208,186 | 6/1980 | Patel | 23/230 |
| 4,212,153 | 7/1980 | Kyonieus et al. | 368/88 |
| 4,264,708 | 4/1981 | Chambers et al. | 430/278 |
| 4,276,190 | 6/1981 | Patel | 252/408.1 |
| 4,373,032 | 2/1983 | Preziozi et al. | 521/38 |
| 4,407,960 | 10/1983 | Tratnyek | 116/207 |
| 4,466,941 | 8/1984 | Cerami et al. | 422/57 |
| 4,526,752 | 7/1985 | Perlman et al. | 422/56 |
| 4,576,795 | 3/1986 | Bruso | 422/61 |

FOREIGN PATENT DOCUMENTS

| | | | |
|---|---|---|---|
| 0117390 | 9/1984 | European Pat. Off. | 116/206 |
| 0046186 | 4/1979 | Japan | 422/58 |

OTHER PUBLICATIONS

Richard Seltzer, "Indicator for Perishable Products Developed", C & EN, 9-29-86.
Shelf Life Estimation of Beverage and Food Products Using Bar Coded Time-Temperature Indicator Labels.
J. V. Crivello, Polymer Eng. & Sci., 23,953, (1983).
J. V. Crivello et al., J. Polymer Sci., Symposium Nw., 56,383, (1976).
S. Maslowski, Appl. Optics, 13,857, (1974).
*Neblette's Handbook of Photography and Reprography Materials, Process and Systems*, John M. Sturge, 7 Ed., (date unknown).
R. N. Macnair, J. Org. Chem., 33, 1945, (1968).

*Primary Examiner*—William A. Cuchlinski, Jr.
*Assistant Examiner*—W. Morris Worth
*Attorney, Agent, or Firm*—Arthur J. Plantamura

[57] ABSTRACT

An activatable time-temperature indicator consists of an oxygen-sensitive reaction product of a triarylmethane dye and a decolorant that is coated on a substrate and covered by an oxygen barrier. Optionally, an oxygen-permeable layer is between the coating and the oxygen barrier. The indicator is activated by removing the oxygen barrier. Following this activation step, a progressive color development occurs at a rate that increases with temperature. The indicator is useful for monitoring the freshness of perishable products, particularly those stored at sub-ambient temperature.

20 Claims, 2 Drawing Sheets

ACTIVATABLE TIME-TEMPERATURE INDICATOR

This application is a continuation of application Ser. No. 815,696, filed Jan. 2, 1986 now abandoned.

BACKGROUND OF THE INVENTION

1. Field of the Invention.

This invention relates to a time-temperature indicator and, more particularly, to an indicator that is inactive until it is activated by removing an oxygen barrier.

2. Description of the Prior Art.

Several patents have disclosed the use of color-changing indicators to monitor the time-temperature history of perishables. Among these are U.S. Pat. No. 4,189,399, issued Feb. 19, 1980, to Patel; and U.S. Pat. No. 4,212,153, issued July 15, 1980, to Kydonieus et al.

When the perishable to be monitored has a short useful lifetime and/or requires refrigeration, then it is desirable, if not essential, to use an indicator that is inactive until activated. Patel, U.S. Pat. Nos. 4,208,186, issued June 17, 1980, and 4,276,190, issued June 30, 1981, disclosed diacetylenic compositions having an inactive form that is activated by contact with an activating vapor. Activation of a diacetylenic monomer in salt form by conversion to the acid form was disclosed in U.S. Pat. No. 4,373,032, issued Feb. 9, 1983, to Preziosi et al.

U.S. Pat. No. 3,768,976, issued Oct. 30, 1973, to Hu et al., has disclosed a temperature-time integrating indicator that is based on temperature-dependent oxygen diffusion into a package that includes an aqueous solution of a redox dye. The dye is dark in the reduced state and becomes colorless when it is oxidized. A similar indicator, involving a free radical sensitive dye and a peroxide on a carrier, was disclosed in U.S. Pat. No. 3,966,414, issued June 29, 1976, to Khattab et al.

Dreyer and Harries (Final Report, Contract DA-19-129-AMC-112(N), U.S. Army Natick Laboratories, Natick Mass., February 1963) observed thermochromism in triphenylmethane leucosulfite solutions. However, they found that aqueous malachite green solutions became nonthermochromic when heated or irradiated in open vessels (see also R. N. Macnair, J. Org. Chem. 33, 1945 (1968)).

SUMMARY OF THE INVENTION

In accordance with the present invention, an activatable time-temperature indicator comprises:

(a) a substrate on which is a coating of an oxygen-sensitive reaction product of a triarylmethane dye and a decolorant for the dye and (b) a removable oxygen barrier over the coating. Preferably, the coating also includes a binder.

In operation, the present invention provides a method of measuring an incremental time-temperature exposure, which comprises the steps:

(a) removing the oxygen barrier from the indicator described above to render it thermally active, (b) measuring the reflectivity of the indicator at a specified wavelength, (c) measuring the reflectivity of the indicator at the specified wavelength after the incremental time-temperature exposure, and (d) calculating the incremental time-temperature exposure by using a pre-established relationship between a change in reflectivity of the indicator and time-temperature exposure.

The process is particularly useful for measuring the exposure of a perishable article, which involves first applying to the article an activatable time-temperature indicator and then following the steps set forth above.

The term "time-temperature indicator," as it is used in the present specification and claims, refers to a composition that responds in a measurable and predictable way to the integrated effect of time and temperature.

DETAILED DESCRIPTION OF THE INVENTION

Figure 1:
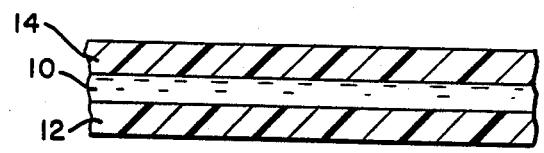
FIG. 1 is a cross section through an indicator of the present invention.

Many articles of commerce—both food and non-food—are perishable. Particularly when the perishable is enclosed in packaging, it may not be readily apparent when the article has exceeded its useful lifetime. It is even more difficult to determine precisely where an article is positioned on an imaginary graph that plots its deterioration as a function of time. Since the rate at which a perishable deteriorates is generally a function of its integrated time-temperature exposure at least within a restricted range of time-temperature a time-temperature indicator is a useful tool for those who are concerned with the freshness of perishable products. The indicator must comprise a composition that provides a readily-measurable physical property that changes in a reproducible way with exposure to time-temperature. For convenience, we use color, but other properties are also suitable. For a real-time indicator, the time frame over which the color changes, in the temperature range of interest, must correspond to that over which the perishable product deteriorates.

For products that undergo significant changes over relatively short times (a few days, for example) or at relatively low temperatures (zero degrees Celsius or below, for example) some form of controlled activation is required to assure that color change does not begin until the desired point in time. One way of activating is to remove an oxygen barrier from an oxygen-sensitive indicator; i.e., an indicator that responds to oxygen exposure in a way that is readily measured and that depends in a predictable way on integrated time-temperature exposure.

We have discovered that triarylmethane dyes that have been decolorized with a reducing agent regain their colored state on exposure to oxygen. Moreover, the rate of color development depends in a predictable way on the integrated time-temperature exposure. Thus, an activatable indicator comprises a decolorized dye, coated on a substrate and covered with a removable oxygen barrier. Alternatively, a coating of decolorized dye may be formed on absorbent paper simply by dipping the paper in a solution of the dye and decolorant or by pouring such a solution over the paper.

To achieve good coating quality, an appropriate binder medium may be added to a decolorized dye solution and coated onto a non-absorbent substrate. In order that the indicator be inactive until the oxygen barrier is removed, it is generally important that the substrate be substantially oxygen impermeable, as well. Of course, many materials satisfy those requirements, but thermoplastics, paper, and metals are preferred substrate materials. A preferred binder is polyvinyl alcohol, which can be coated from an aqueous solution. Obtaining good quality coatings requires proper matching of coating and substrate, using criteria that are well known in the coating art.

Any suitable method may be used to apply the coating to a substrate, including spraying (e.g., with an airbrush) or coating with a doctor knife or Mayer rod. Depending on the coating method used, it may be necessary to control the viscosity of the solution by, for example, the molecular weight of the binder.

The dyes suitable for use in the present invention are triarylmethane dyes, which have the general structure:

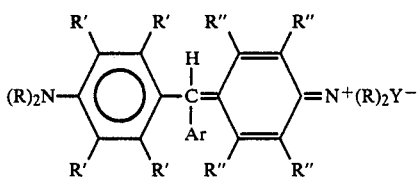

Each R is independently H, $(C_1-C_2)$alkyl, hydroxyalkyl, sulfonated alkyl, or a substituted phenyl group. R' is independently H, $C_1$-alkyl, or a sulfite group. Each R'' is independently H or $C_1$-alkyl. Ar is

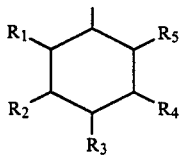

where $R_1-R_5$ are independently H, $(C_1-C_4)$alkyl, halogen, amine, $N(C_1-C_4)$alkyl, carboxylic acid, sulfite, hydroxyl, or a substituted phenyl group. Ar may also be replaced by naphthalene or substituted naphthalenes, in which case the dye is a diphenylnaphthylmethane dye. $Y^-$ is an anion, such as bisulfate, halide, oxalate, etc. Detailed information concerning these dyes—preparation, properties, etc.—appears in K. Venkataraman, *The Chemistry of Synthetic Dyes*, Vol. II, Academic Press, N.Y., 1952, pp 705 ff.

By choosing from among various dyes and mixtures of two or more, a wide variety of final (i.e., after time-temperature exposure) colors can be obtained. For the present invention, the preferred dyes are brilliant green, malachite green, crystal violet, and mixtures of these dyes. More preferably, the dye includes brilliant green.

Decolorants suitable for this invention are generally reducing agents such as bisulfites, hydroxides, cyanides, and hydrogen. Preferably the decolorant is an alkali metal- or ammonium-bisulfite, more preferably sodium bisulfite.

There are two distinct categories of oxygen barrier - cover sheets and oxygen-impermeable overcoats. Cover sheet materials are preferably thermoplastics, more preferably those that may be laminated or heat-sealed to the substrate. The indicator is activated by separating the cover sheet from the coating.

Many film-forming oxygen-impermeable materials that are well known in the art may be used to overcoat the coating of this invention and serve as an oxygen barrier. Preferably, the overcoat is soluble in an organic solvent that does not dissolve the coating, and the indicator is activated by dissolving the overcoat.

FIG. 1 is a cross-sectional view of a time-temperature indicator of the present invention. Decolorized dye 10 is sandwiched between substrate 12 and removable oxygen barrier 14. Both substrate 12 and oxygen barrier 14 are hatched to show their composition to be plastic, but any suitable, substantially oxygen-impermeable material will do. They may be of the same or different materials. Oxygen barrier 14 may be a soluble overcoat, as was discussed above.

A primary application of the present invention is to monitor the freshness of perishable articles. Since different perishable articles deteriorate at different rates, at a particular storage temperature, it is useful to have indicators that likewise develop color at different rates. The rate of color development in indicators can be controlled in two independent ways direct and indirect.

A direct route to controlling the rate of indicator color development is through indicator composition. Thus, the rate of color development may be controlled by the composition and concentration of the dye, composition and amount of decolorizing agent, and coating weight of decolorized dye.

An indirect route to controlling color development uses an intermediate oxygen-permeable layer between the decolorized dye and the oxygen barrier. If the rate of indicator color development is too rapid when it is exposed to ambient atmosphere, the rate can be reduced by using an oxygen-permeable layer. As with the oxygen barrier, the oxygen-permeable layer may be in the form of a coating or a cover sheet. In either case, the permeable layer is not removed with the oxygen barrier, but remains as part of the indicator. If the oxygen-permeable layer is a cover sheet, permeability can result from the inherent nature of the sheet and/or from holes in the sheet. A uniform pattern of small holes can be provided conveniently by embossing rollers or other methods well known in the art. Oxygen-permeable materials for an intermediate layer may be selected from a variety of suitable materials, including thermoplastics, such as low density polyethylene, various silcone polymers, etc.

Figure 2:
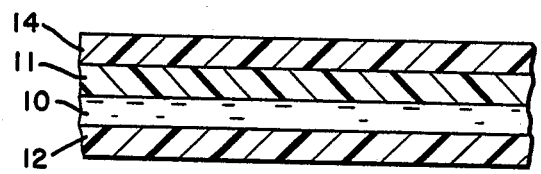
FIG. 2 is a cross section through another embodiment of the indicator of the present invention.

FIG. 2 is a cross-sectional view of a time-temperature indicator that includes an oxygen-permeable layer 11 between the decolorized dye 10 and removable oxygen barrier. Although hatched to show its composition to be plastic, any suitable, oxygen-permeable material may be used, and it may be in the form of an overcoat.

Both the substrate and the oxygen barrier should be relatively oxygen-impermeable. Many references provide data on oxygen permeability and can help to guide in selecting appropriate materials for both oxygen-permeable and -impermeable layers (see e.g., Robb, in *Materials in Biomedical Engineering*, edited by E. M. Weyer (Vol. 146 of Annals of the N.Y. Academy of Sciences, N.Y., 1968), p 119). Polyester, which is among the thermoplastics that have low oxygen permeability, is also heat-sealable. It is a good material for both the substrate and the cover sheet of the present invention.

As was discussed above, a particularly simple way to demonstrate the present invention is to dip absorbent paper into a decolorized dye solution In that case, it may be convenient to seal the paper, after dipping, between a pair of permeable layers and them between a pair of impermeable layers.

Figure 3:
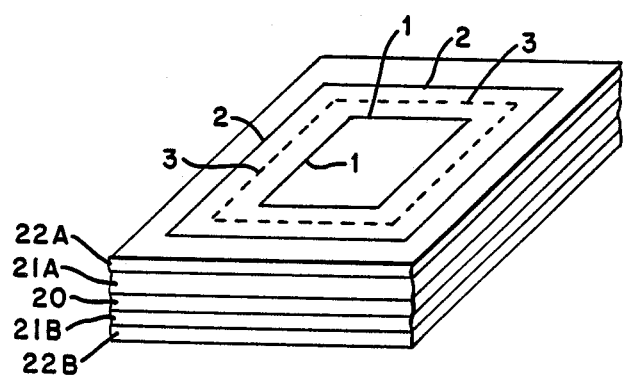
FIG. 3 depicts an easily-demonstrated indicator of the present invention.

FIG. 3 depicts this embodiment, where absorbent paper 20, permeated with decolorized dye, is sandwiched between permeable layers 21A and 21B, which in turn are sandwiched between oxygen barriers 22A and 22B. If the perimeter 1 of the permeable layer seal is completely enclosed by the perimeter 2 of the oxygen barrier seal, then the indicator may be activated by simply cutting along a path between the two perimeters (dashed line 3) and removing barrier layers 22A and 22B.

The following examples are presented in order to provide a more complete understanding of the invention. The specific techniques, conditions, materials, and reported data set forth to illustrate the principles and practices of the invention are exemplary and should not be construed as limiting the scope of the invention.

EXAMPLE 1

A solution of 55 mg of brilliant green (Kodak,C624 M.W. 482.64) dye in 10 ml of distilled water was decolorized by dropwise adding to the dye solution a solution of 300 mg of sodium bisulfite dissolved in 3 ml distilled water. Strips of filter paper were impregnated with the fresh decolorized solution and, while still moist, each was laminated as follows to form indicator labels:

A coated strip was thermally sealed between two sheets of 50 micrometer thickness oxygen-permeable low density polyethylene film (cut from bags manufactured by Linco Industries, New York). The laminated sheet of filter paper was further thermally sealed between two sheets of 100 micrometer polyester film, which is substantially impermeable to oxygen.

Initial reflectivity ranged from 85–90% for all these laminated labels. Some of the labels were stored at room temperature to determine the activity of unactivated labels. All laminated strips remained colorless for days; i.e., they were inactive.

Figure 4:
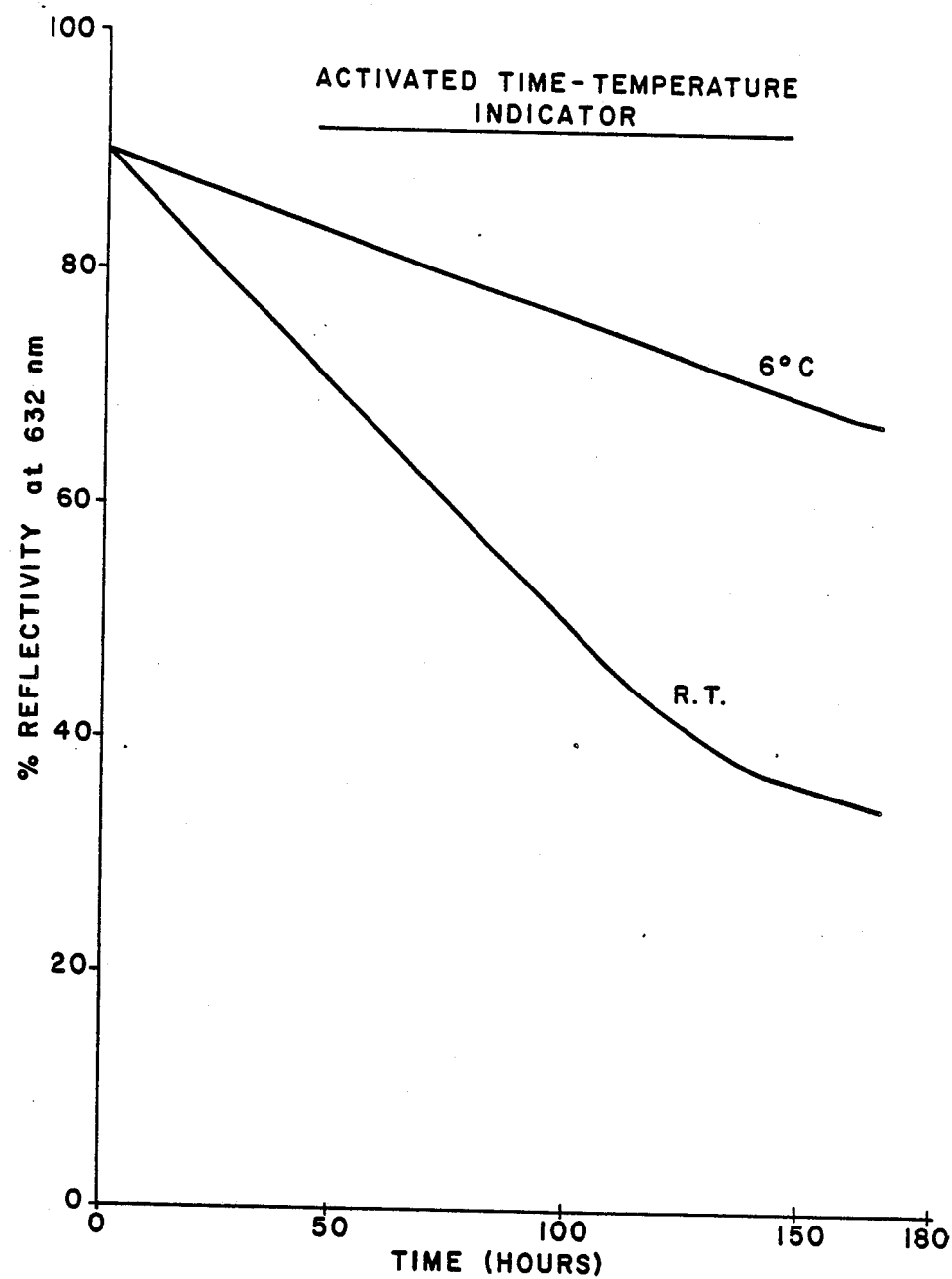
FIG. 4 depicts the time dependence of reflectivity at 632 nm of an activated indicator label of the present invention held at room temperature and at 6° C.

After the labels were activated by removing the outer lamination (oxygen barrier), progressive color development was observed. Color development was monitored by measuring the decrease in reflectivity (at 632 nm) with time at a specified temperature. Over a period of time, the reflectivity of the indicator label decreased at a temperature-dependent rate. FIG. 4 depicts results for labels stored at room temperature and at 6° C.

EXAMPLE 2

Example 1 was repeated using each of malachite green dye and crystal violet dye in place of the brilliant green dye of Example 1. Essentially the same time-temperature effects were observed.

EXAMPLE 3

Example 1 was repeated using each of sodium cyanide solution and sodium hydroxide solution instead of sodium bisulfite as the reducing agent. The dyes were readily decolorized; however, activated labels did not develop color densities as high (i.e., reflectance as low) as with the labels decolorized with bisulfite.

EXAMPLE 4

Example 1 was repeated, except that the decolorized solution was mixed with polyvinyl alcohol gel in water and the resulting mix was airbrushed onto different substrates, such as plastics, metals and glass. Time-temperature effects similar to Example 1 were observed when activated coated strips (exposed to laboratory atmosphere) were monitored.

EXAMPLE 5

Much faster color development was observed when the polyethylene inner lamination film was replaced by a more oxygen-permeable silicone membrane (75 micrometer thickness).

I claim:

1. An activatable time-temperature indicator comprising:
   (a) a substrate on which is a coating of an oxygen-sensitive reaction product of a triarylmethane dye and a decolorant for the dye and
   (b) a removable oxygen barrier over the coating.

2. The indicator of claim 1 in which the substrate material is absorbent paper.

3. The indicator of claim 1 in which the substrate material is substantially oxygen-impermeable and is selected from the group consisting of thermoplastics, paper, and metals.

4. The indicator of claim 1 in which the coating further comprises a binder.

5. The indicator of claim 4 in which the binder comprises polyvinyl alcohol.

6. The indicator of claim 4 in which the substrate material is a thermoplastic.

7. The indicator of claim 1 in which the triarylmethane dye is selected from one or more of the group consisting of brilliant green, malachite green, and crystal violet.

8. The indicator of claim 7 in which the triarylmethane dye includes brilliant green.

9. The indicator of claim 1 in which the decolorant is a reducing agent selected from the group consisting of bisulfites, hydroxides, cyanides, and hydrogen.

10. The indicator of claim 9 in which the decolorant is selected from the group consisting of alkali metal- and ammonium-bisulfites.

11. The indicator of claim 2 further comprising a first oxygen-permeable layer between the coating and the oxygen barrier and a second oxygen-permeable layer between the substrate and a second oxygen barrier.

12. A method of measuring an incremental time-temperature exposure with an activatable time-temperature indicator comprising a substrate on which is a coating of oxygen-sensitive reaction product of a triarylmethane dye and decolorant for the dye and a removable oxygen barrier over the coating, which comprises the steps of:
   (a) removing the oxygen barrier from the indicator to expose the indicator to ambient oxygen, thereby activating it,
   (b) measuring the reflectivity of the indicator at a specified wavelength,
   (c) measuring the reflectivity of the indicator at the specified wavelength after an incremental time-temperature exposure, and
   (d) calculating the incremental time-temperature exposure by using a pre-established relationship between a change in reflectivity of the indicator and time-temperature exposure.

13. The method of claim 12 in which the coating further comprises a binder.

14. The method of claim 12 in which the substrate material is a thermoplastic.

15. The method of claim 12 in which the triarylmethane dye includes malachite green.

16. The method of claim 12 in which the decolorant is selected from the group consisting of alkali metal- and ammonium-bisulfites.

17. The method of claim 12 in which the oxygen barrier comprises a thermoplastic cover sheet that is separated from the coating to activate the indicator.

18. The method of claim 12 in which the oxygen barrier comprises an overcoat that is dissolved to activate the indicator.

19. The method of claim 12 in which the temperature exposure is in the range between about −20° and 60° C.

20. A method of measuring an incremental time-temperature exposure of a perishable article by (a) applying to the article an activatable time-temperature indicator comprising a substrate on which is a coating of an oxygen sensitive reaction product of a triarylmethane dye and a decolorant for the dye and a removable oxygen barrier over the coating, (b) removing the oxygen barrier from the indicator to expose it to ambient oxygen, thereby activating it, (c) measuring the reflectivity of the indicator at a specified wavelength, (d) measuring the reflectivity of the indicator at the specified wavelength after incremental time-temperature exposure, and (e) calculating the incremental time-temperature exposure by using a pre-established relationship between a change in reflectivity of the indicator and time-temperature exposure.

* * * * *